US009003859B2

(12) United States Patent
Paris et al.

(10) Patent No.: US 9,003,859 B2
(45) Date of Patent: Apr. 14, 2015

(54) BENDING INSTRUMENT AND METHODS OF USING SAME

(75) Inventors: Anthony James Paris, Anchorage, AK (US); Gan Wu, Houston, TX (US); Brian Patrick Glasheen Jr., Anchorage, AK (US); Jacob Thompson, Eagle River, AK (US)

(73) Assignee: University of Alaska Anchorage, Anchorage, AK (US)

( * ) Notice: Subject to any disclaimer, the term of this patent is extended or adjusted under 35 U.S.C. 154(b) by 1017 days.

(21) Appl. No.: 13/078,546

(22) Filed: Apr. 1, 2011

(65) Prior Publication Data
US 2012/0247173 A1     Oct. 4, 2012

(51) Int. Cl.
*B21D 7/06* (2006.01)
*B21F 1/00* (2006.01)
*A61B 17/88* (2006.01)
*A61B 17/70* (2006.01)

(52) U.S. Cl.
CPC ............. *B21F 1/002* (2013.01); *A61B 17/8863* (2013.01); *B21D 7/063* (2013.01); *A61B 17/7013* (2013.01)

(58) Field of Classification Search
CPC .......... B21F 1/002; B21D 7/06; B21D 7/063; B21D 7/08
USPC ........... 72/149, 156, 159, 170, 172, 216, 217, 72/387, 388, 409.01, 409.11
See application file for complete search history.

(56) References Cited

U.S. PATENT DOCUMENTS

| | | | | | |
|---|---|---|---|---|---|
| 1,762,234 | A | * | 6/1930 | Matthews | 72/218 |
| 3,447,353 | A | * | 6/1969 | Noveske | 72/217 |
| 3,662,580 | A | * | 5/1972 | Power | 72/217 |
| 3,785,190 | A | * | 1/1974 | Schall et al. | 72/149 |
| 4,052,879 | A | * | 10/1977 | Crees | 72/318 |
| 4,428,216 | A | * | 1/1984 | Fling | 72/156 |
| 4,587,824 | A | * | 5/1986 | Wiersema et al. | 72/217 |
| 4,608,888 | A | * | 9/1986 | Rommel | 81/313 |
| 4,785,650 | A | | 11/1988 | Lusty | 72/217 |
| 4,986,104 | A | * | 1/1991 | Caporusso et al. | 72/158 |
| 5,389,099 | A | | 2/1995 | Harmeister et al. | 606/61 |
| 5,431,035 | A | | 7/1995 | Sheen | 72/133 |
| 5,490,409 | A | | 2/1996 | Weber | 72/458 |
| 5,548,985 | A | | 8/1996 | Yapp | 72/149 |
| 6,035,691 | A | | 3/2000 | Lin et al. | 72/413 |
| 7,234,338 | B2 | * | 6/2007 | Mirtz et al. | 72/459 |

(Continued)

OTHER PUBLICATIONS

LaRusso, L. (2013). *Spinal Fusion*. Retrieved Jan. 4, 2013, from CVS Pharmacy Health Resources: http://health.cvs.com/GetContent.aspx?token=f75979d3-9c7c-4b16-af56-3e122a3f19e3&chunkiid=102862.

(Continued)

*Primary Examiner* — Edward Tolan
(74) *Attorney, Agent, or Firm* — Ballard Spahr LLP

(57) ABSTRACT

A bending instrument is disclosed having first and second lever assemblies. The first lever assembly has a first lever and a first bending member, and the second lever assembly has a second lever that is configured for pivotal motion relative to the first lever. The bending instrument also has a gear assembly that is rotatively coupled to a distal portion of the first lever and which defines a lobe on which a second bending member is mounted. The second bending member of the gear assembly is configured to be angularly rotated upon the pivotal rotation of the second lever relative to the first lever.

24 Claims, 7 Drawing Sheets

(56) References Cited

U.S. PATENT DOCUMENTS

| | | |
|---|---|---|
| 7,302,887 B1 | 12/2007 | Chapman et al. ............ 100/234 |
| 7,454,939 B2 | 11/2008 | Garner et al. .................. 72/459 |

OTHER PUBLICATIONS

Mohan Lalith, A., & Das, K. (2003). *History of Surgery for the Correction of Spinal Deformity: Modern Era of Spinal Instrumentation*. Retrieved Jan. 4, 2013, from www.medscape.com: http://www.medscape.com/viewarticle/448306_print.

North America Spine Society (2009) *Spinal Fusion*. Retrieved Jan. 4, 2013, from http://www.knowyourback.org/Pages/Treatments/SugicalOptions/SpinalFusion.aspx.

Paris, A.J. (2005). *A study on the Biomechanical Behavior of Spinal Fixation assemblies with Stainless Steel and Titanium Rods in a Vertebrectomy Model Phase II: The Effect of Lordosis*. Boise: Department of Mechanical Engineering Boise State University.

*The History of Lumbar Spine Stabilization*. (n. d.). Retrieved Jun. 22, 2012, from The Burton Report: http://www.burtonreport.com/InfSpine/SurgStabilSpineHistory.htm.

\* cited by examiner

BENDING INSTRUMENT AND METHODS OF USING SAME

FIELD OF THE INVENTION

This invention relates to a bending instrument and, more specifically, to a hand-held instrument for bending a surgical implant.

BACKGROUND

Approximately 500,000 Americans undergo spinal surgery each year, and the instrumentation involved in these surgeries has and will continue to evolve. This evolution not only includes the advancement of the material properties of the implants themselves, but also the advancements of the surgical tools used by surgeons.

Correction of spinal instability, whether due to traumatic injury or disease, is often accomplished through spinal surgery and the use of instrumentation to reduce relative motion between two or more vertebrae. This procedure can be approached from the back (posterior), front (anterior) or by a combination of posterior and anterior approaches. Metallic instrumentation is often used to stabilize the spine. These metallic implants conventionally consist of wires, screws, hooks and rods. A metal rod is bent to match the desired curvature of the spine and is attached to the vertebra with wire, screws, or hooks to correct any deformity, thereby providing support to the spine. There are a variety of conventional surgical rod benders that can be used to shape spinal rods. Existing spinal rod benders can be broken up into two groups: table-top benders and hand-held benders.

The most commonly used hand-held bender is the French Bender, which is a cam-action rod bender that uses three points of contact for bending. The French Bender is capable of making bends up to approximately 30 degrees. To operate the French Bender the surgeon must place the rod in the desired position and then grasp two handles and bring them together. This operation resembles that of a bolt cutter and sometimes requires another individual to hold the rod in place so that the rod doesn't fall out of the desired position while the surgeon grasps the handles. Alternatively, the other individual grasps the handles of the rod bender, and the surgeon instructs the other individual where, and to what extent, the rod should be bent. This procedure is less than optimal because the surgeon often uses the device with the assistance of additional personnel. The extra communication required between the surgeon and staff produces potential inefficiencies and inaccuracies in the bending of the rod. Additionally, the action of bringing the handles of the bender together has caused surgeons to accidentally injure themselves. Another hand-held surgical bender is the In Situ Bender or Key Hole Bender, which is used to correct the curvature of the rod after it is placed into the construct of the spinal system.

A variety of conventional table-top benders are available for surgical applications. The procedure for operating these benders is a multi-step process which can be quite tedious and time-consuming—the surgeon must leave the patient's side, approach the table with the rod bender, bend the rod, and then return to the patient. This procedure is often repeated multiple times to bend the rod to the ideal shape for the patient's spine. In general, table-top benders offer greater precision (at bending angles of up to 90 degrees) and repeatability at the cost of decreased efficiency.

Thus, there is a need in the pertinent art for a hand-held bending instrument that can provide precise bends at a desired bending angle while having an ergonomic, safe, and efficient design.

SUMMARY

Described herein is a bending instrument comprising first and second lever assemblies. The first lever assembly can have a first lever and a first bending member that is mounted on a distal portion of the first lever. The second lever assembly has a second lever that defines a channel on its distal end. In one aspect, the second lever is configured for pivotal motion relative to the first lever. The bending instrument also comprises a gear assembly that is rotatively coupled to the distal portion of the first lever and that can be configured for rotation about a common axis, i.e., an axis that is common to the longitudinal axis of the first bending member. The gear assembly defines a lobe on which a second bending member is mounted. In one aspect, the second bending member is configured so that it's longitudinal axis extends along an axis substantially parallel to the common axis. In a further aspect, at least a portion of the gear assembly can be mounted therein the channel of the distal end of the second lever.

In operation, the second bending member of the gear assembly can selectively be angularly rotated about the common axis and angularly rotated relative to and about the first bending member upon the pivotal rotation of the second lever relative to the first lever. Methods of using the bending instrument are also described.

BRIEF DESCRIPTION OF THE FIGURES

These and other features of the preferred embodiments of the invention will become more apparent in the detailed description in which reference is made to the appended drawings wherein.

DETAILED DESCRIPTION

Figure 1:
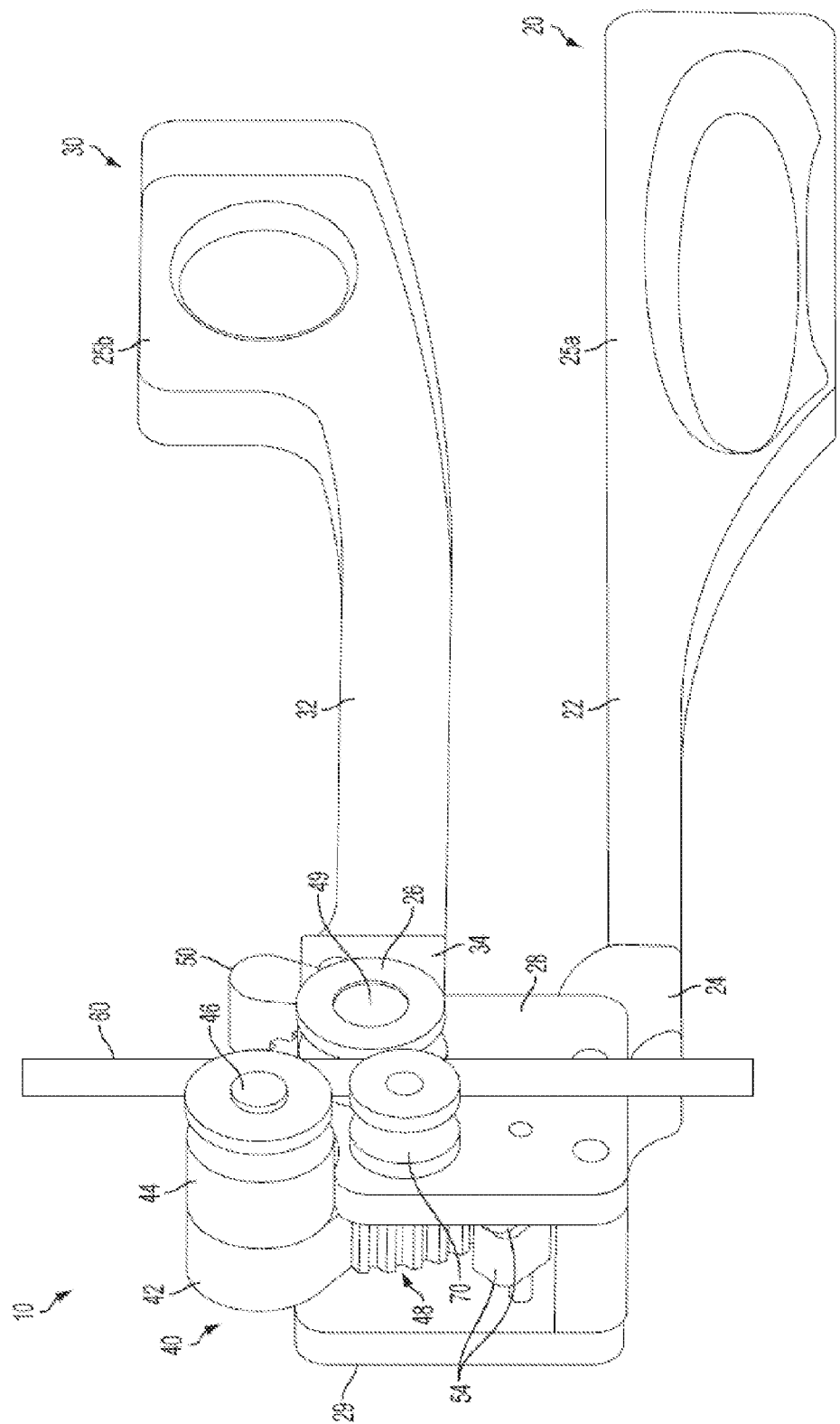
FIGS. 1 and 2 are perspective views of one embodiment of a bending instrument as described herein.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a surgical implant" can include two or more such surgical implants unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

In one embodiment, and with reference to FIGS. 1-7, the invention relates to a bending instrument 10. In one aspect, as depicted in FIGS. 1, 3-4, and 6-7, the bending instrument 10 can comprise a first lever assembly 20. Optionally, in this aspect, and as shown in FIGS. 1-6, the first lever assembly 20 can comprise a first lever 22 and a first bending member 26. It is contemplated that the first bending member 26 can be mounted thereon a distal portion 24 of the first lever 22. In one aspect, as depicted in FIGS. 1-6, the distal portion 24 of the first lever 22 can comprise a first side wall 28. In another aspect, the first bending member 26 can have a longitudinal axis $A_{FBM}$. In this aspect, the first bending member 26 can be mounted to the first lever 22 such that the longitudinal axis $A_{FBM}$ of the first bending member extends substantially perpendicular to the first side wall 28 of the first lever.

In another aspect, as shown in FIGS. 1, 3-4 and 6-7, in another aspect, the bending instrument 10 can comprise a second lever assembly 30, which can comprise a second lever 32. In an additional aspect, the second lever 32 can have a distal end 34 that defines a channel 36. In one non-limiting example, it is contemplated that the channel 36 of the distal end 34 of the second lever 32 can comprise a U-shaped channel. Optionally, in another aspect, the second lever 32 can be configured for pivotal motion relative to the first lever 22. Alternatively, it is contemplated that the first lever 22 can be configured for pivotal motion relative to the second lever 32.

Figure 2:
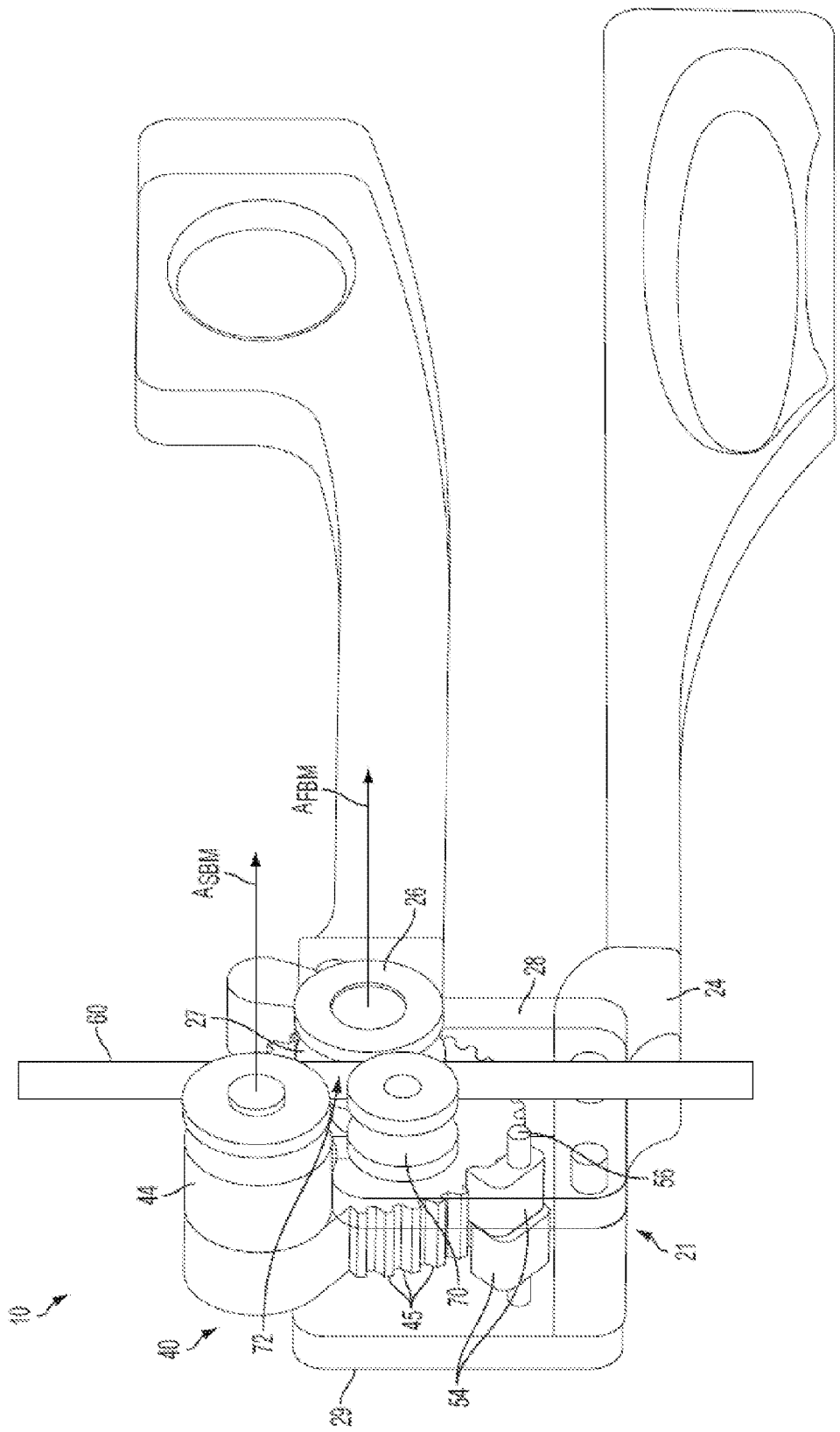

In a further aspect, and with reference to FIGS. 1-6, the bending instrument 10 can comprise a gear assembly 40 that can optionally be rotatively coupled to the distal portion 24 of the first lever 22. As shown in FIG. 2, it is contemplated that the gear assembly 40 can be configured for rotation about a common axis $A_C$, i.e., an axis that is common to the longitudinal axis $A_{FBM}$ of the first bending member 26. In another aspect, the gear assembly 40 can define a lobe 42. In an additional aspect, the gear assembly 40 can have a second bending member 44 that can be mounted thereon a portion of the lobe 42. For example, and without limitation, it is contemplated that a conventional pin 46 can be positioned within and secured thereto aligned openings defined therein the lobe 42 and the second bending member 44. It is further contemplated that the second bending member 44 can extend substantially perpendicular to the lobe 42. As shown in FIG. 2, it is still further contemplated that the longitudinal axis $A_{SBM}$ of the second bending member 44 can extend along an axis substantially parallel to the common axis $A_C$. In still an additional aspect, it is contemplated that at least a portion of the gear assembly 40 can optionally be mounted therein the channel 36 of the distal end 34 of the second lever 32.

In still a further aspect, the bending instrument 10 can comprise means for angularly rotating the second bending member 44 of the gear assembly 40 about the common axis $A_C$ and relative to and about the first bending member 26 upon the pivotal rotation of the second lever 32 relative to the first lever 22.

In one aspect, and with reference to FIGS. 1 and 3-5, the gear assembly 40 can have a gear surface 48 on at least a portion of its peripheral edge. In this aspect, the gear surface 48 of the gear assembly 40 can define a plurality of teeth 45.

In exemplary aspects, and with reference to FIGS. 1-6, it is contemplated that the means for angularly rotating the second bending member 44 can comprise a drive pawl 50 that is sized and shaped for complementary engagement with the gear surface 48 of the gear assembly 40. Optionally, in one aspect, the drive pawl 50 can be rotatably mounted therein the channel 36 of the distal end 34 of the second lever 32. In this aspect, it is contemplated that the drive pawl 50 can define an opening that is configured to receive a conventional pin 52 that extends across the channel 36 and is secured thereto the distal end 34 of the second lever 32.

Optionally, in an additional aspect, the second lever 32 can be configured for pivotal motion relative to the first lever 22 between an open position and a closed position. In this aspect, it is contemplated that, when the second lever 32 is pivoted relative to the first lever 22 from the open position to the closed position, the drive pawl 50 can selectively and drivingly engage a tooth 45 of the gear assembly 40 such that the gear assembly is rotated about the common axis $A_C$ through a defined acute number of degrees. In one aspect, the drive pawl 50 can be biased such that the drive pawl maintains contact with the teeth 45 of the gear assembly 40 as the drive pawl is advanced from one tooth of the gear assembly to consecutive teeth of the gear assembly. In this aspect, the drive pawl 50 can be biased by a spring (not shown) that is configured to rotate the drive pawl about pin 52. In an exemplary, non-limiting aspect, the spring can be a torsion spring.

In another aspect, the bending instrument 10 can comprise means for securely positioning the drive pawl 50 in a disengaged position spaced from the gear assembly 40. In one aspect, it is contemplated that the means for securely positioning the drive pawl 50 in the disengaged position can comprise a conventional spring-ball-detent mechanism. In this aspect, the spring-ball-detent mechanism can be configured to secure the drive pawl 50 in the disengaged position until a user selectively applies a force sufficient to release the spring-ball-detent mechanism and, thereby, permit engagement between the drive pawl and the gear assembly 40. It is contemplated that the means for securely positioning the drive pawl 50 in the disengaged position can comprise any other mechanical mechanism capable of temporarily holding the drive pawl 50 in the disengaged position, including, for example and without limitation, a plunger mechanism, a pop through mechanism, a pin, a ring, and the like. Optionally, the means for securely positioning the drive pawl 50 in the disengaged position can be coupled to the second lever 32.

In an additional aspect, the drive pawl 50 can be operatively coupled to an on/off switch that is moveable about and between an off position and an on position. In this aspect, it is contemplated that a user can direct the drive pawl 50 to engage the gear assembly 40 by movement of the on/off switch from the off position to the on position. In yet another aspect, the drive pawl 50 can be operatively coupled to one or more torsion springs that are configured to maintain engagement between the drive pawl and the gear assembly 40 during operation of the bending instrument 10.

It is further contemplated that the first lever 22 and the second lever 32 can each have a proximal end 25a, 25b that is configured for engagement by at least a portion of a hand of a user. For example, and without limitation, the proximal ends 25a, 25b of the first lever 22 and the second lever 32 can each define at least one opening that is configured to receive one or more fingers of the hand of the user. It is contemplated that the openings in the proximal ends 25a, 25b of the first lever 22 and the second lever 32 can provide the user with better control over the bending instrument 10 and permit the user to easily squeeze the levers together or pull the levers apart.

As shown in FIGS. 1-4, in another aspect, the first lever assembly can comprise the first side wall 28 and a second side wall 29 spaced from the first side wall. In this aspect, it is contemplated that the means for angularly rotating the second bending member 44 can comprise at least one locking pawl 54 spaced from the drive pawl. Optionally, in one aspect, the at least one locking pawl 54 can be mounted between and secured thereto the two spaced side walls 28, 29. In this aspect, it is contemplated that each locking pawl 54 of the at least one locking pawl can define an opening that is configured to receive a conventional pin 56 that extends between, and is secured thereto, the two spaced side walls 28, 29. In a further aspect, the at least one locking pawl 54 can be configured, or otherwise sized and shaped, to selectively operatively engage a portion of the gear surface 48 of the gear assembly 40 as the gear assembly rotates. In this aspect, the at least one locking pawl 54 can operatively engage the gear assembly 40 such that the at least one locking pawl remains engaged with the gear assembly when the second lever 32 is pivoted to the open position.

In an additional aspect, the at least one locking pawl 54 can be operatively coupled to an on/off switch that is moveable about and between an off position and an on position. In this aspect, it is contemplated that a user can direct the at least one locking pawl 54 to engage the gear assembly 40 by movement of the on/off switch from the off position to the on position. It is further contemplated that the on/off switch, which allows for quick, selective engagement or disengagement of the gear assembly 40, can permit a user to more easily produce large-angle bends, as well as small, gradual bends, in a surgical implant 60. In yet another aspect, the at least one locking pawl 54 can be operatively coupled to one or more torsion springs that are configured to maintain engagement between the at least one locking pawl and the gear assembly 40 during operation of the bending instrument 10. It is contemplated that the one or more torsion springs can be positioned such that the gear assembly 40 is returned to a starting position after the gear assembly is released by the at least one locking pawl 54.

Figure 3:
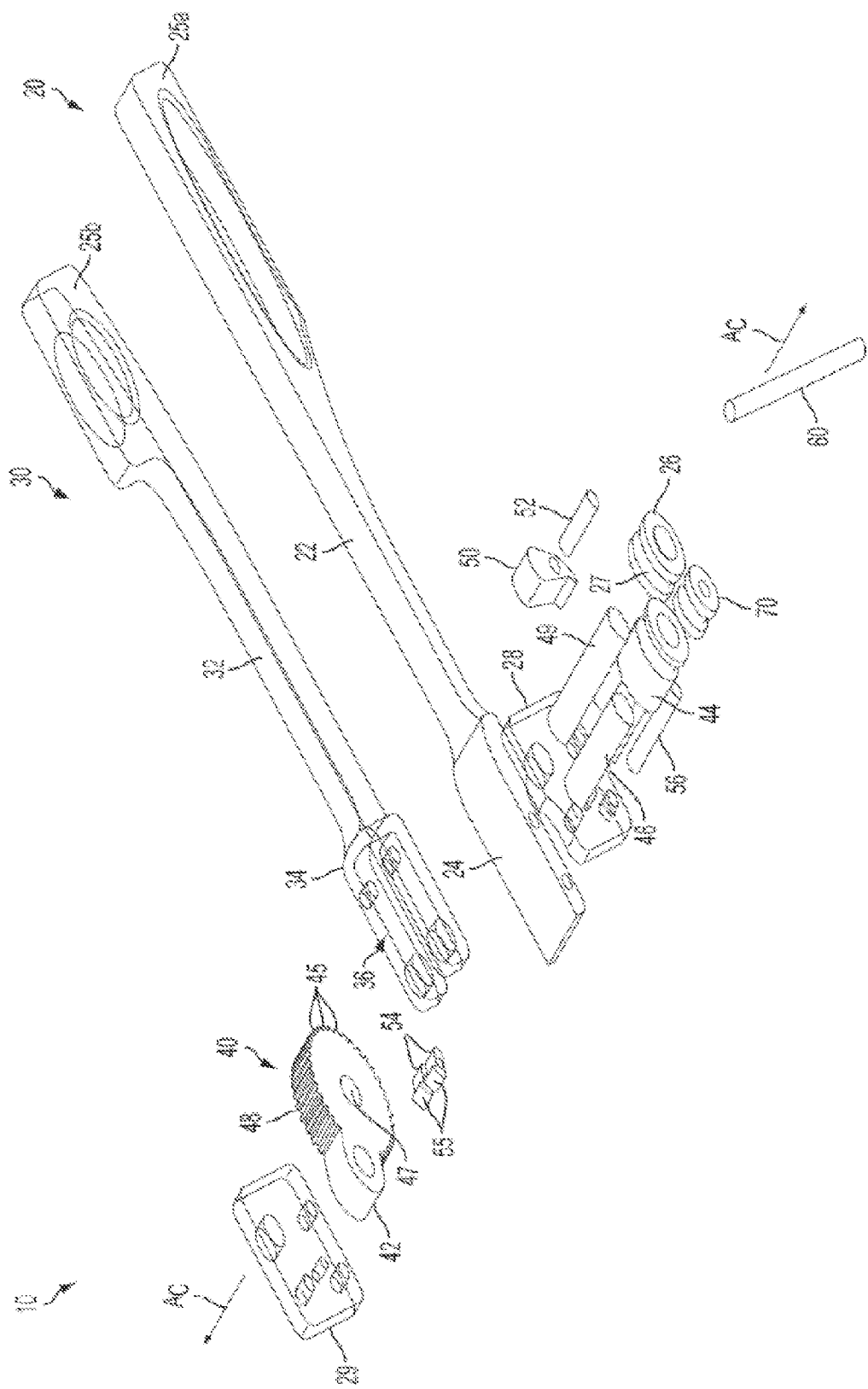
FIG. 3 is an exploded perspective view of the bending instrument of FIGS. 1 and 2.
Figure 4:
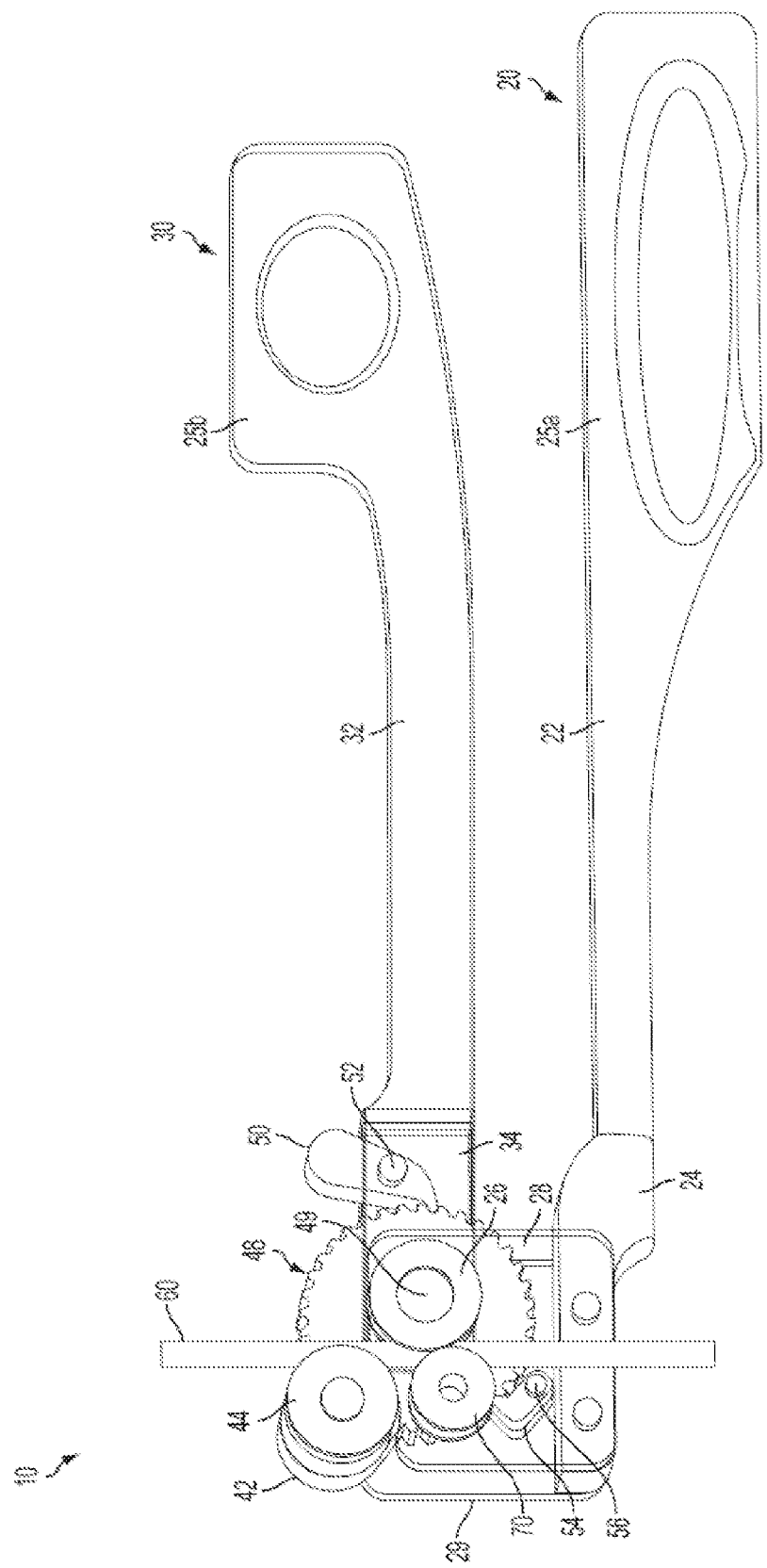
FIG. 4 is a partially transparent, right side view of the bending instrument of FIGS. 1 and 2.
Figure 5:
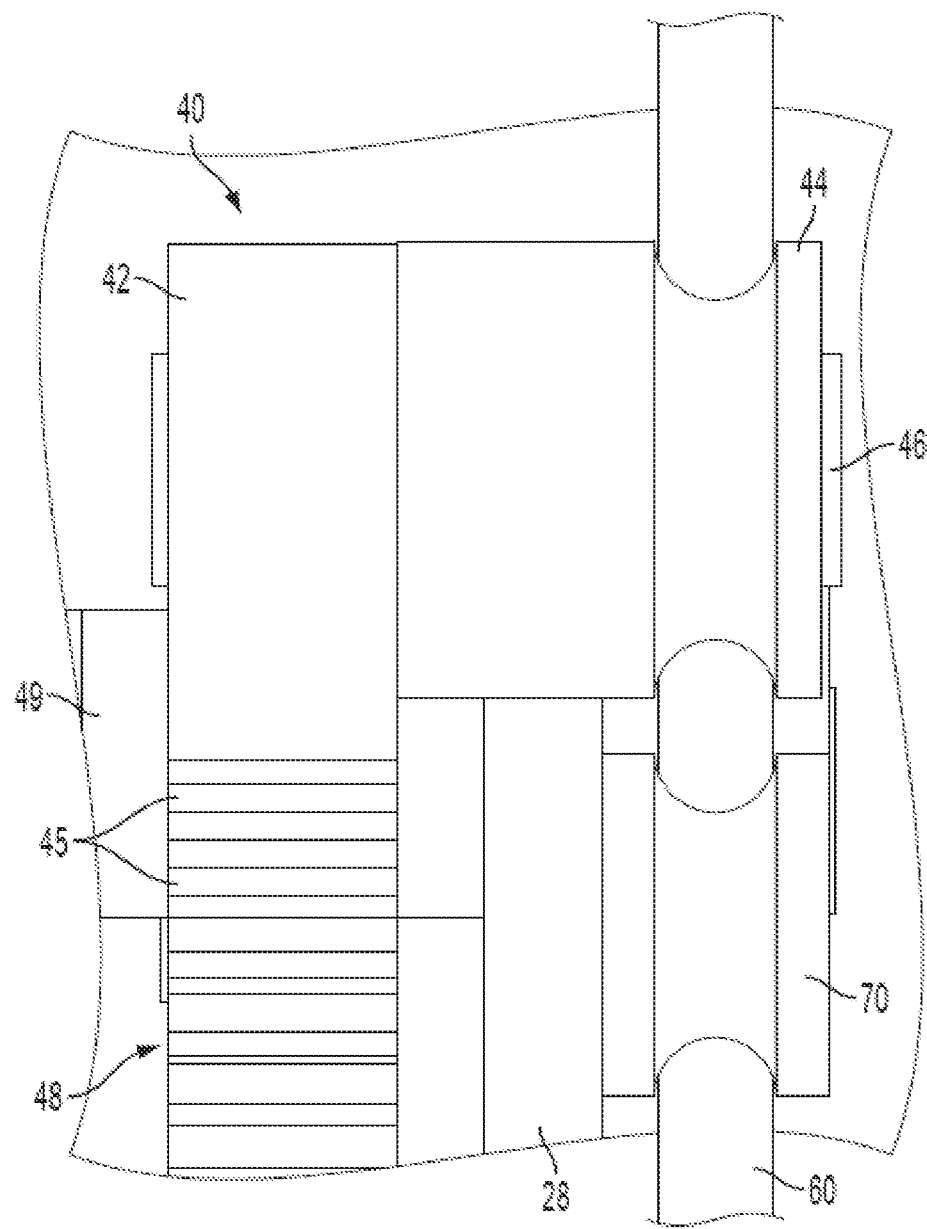
FIG. 5 is a front view of the gear assembly of the bending instrument of FIGS. 1 and 2.

In a further aspect, and with reference to FIG. 3, the distal end 34 of the second lever 32 can optionally define one or more openings that align with a central opening 47 of the gear assembly 40. Optionally, in this aspect, it is contemplated that the openings of the distal end 34 of the second lever 32 and the central opening 47 of the gear assembly 40 can be configured to receive a conventional pin 49 that extends between, and is secured thereto, the two spaced side walls 28, 29 of the first lever assembly 20.

In still a further aspect, as depicted in FIGS. 1-4, it is contemplated that the at least one locking pawl 54 can comprise a first locking pawl and a second locking pawl. In this aspect, it is further contemplated that, during rotation of the gear assembly 40, the first locking pawl and the second locking pawl can be configured for sequential alternating engagement of the plurality of teeth 45 of the gear assembly. In an additional aspect, it is contemplated that each tooth 45 of the plurality of teeth of the gear assembly 40 can be angularly spaced from adjacent teeth along the gear surface 48 such that, after a locking pawl 54 of the at least one locking pawl is engaged by the gear assembly and the first lever 22 and the second lever 32 are positioned in the closed position, a user of the bending instrument 10 can move the first and second levers toward the open position to advance the drive pawl 50 one or more teeth along the gear surface. Accordingly, it is contemplated that the angular spacing between adjacent teeth 45 along the gear surface 48 can be selected in view of the ergonomics of opening and closing the first and second levers 22, 32, which can be dependent upon the lengths of the first and second levers and the size, strength, and dexterity of the fingers and hands of the user of the bending instrument 10.

In a further aspect, the plurality of teeth 45 defined by the gear surface 48 of the gear assembly 40 can have a substantially uniform length. In this aspect, it is contemplated that the first locking pawl and the second locking pawl can each have an engagement portion 55 having a length. It is contemplated that the ratio of the length of the engagement portion of the first locking pawl and the length of the engagement portion of the second locking pawl can range from about 1:1 to about 2:1, and more preferably be about 1.5:1. In an exemplary aspect, the teeth 45 of the gear assembly 40 can be spaced from adjacent teeth along the gear surface 48 by a separation distance, and the engagement portion of first locking pawl can be longer than the engagement portion of the second locking pawl by a length corresponding to about one-half the separation distance. In this exemplary aspect, operationally the angle by which the gear assembly 40 should be rotated to permit full engagement of the gear assembly by a locking pawl is about one-half the angle formed between adjacent teeth 45 of the gear assembly.

In one exemplary non-limiting aspect, each tooth 45 of the plurality of teeth of the gear assembly 40 can be angularly spaced from adjacent teeth along the gear surface 48 by between about 5 degrees and about 15 degrees, and more preferably by about 10 degrees. In these aspects, it is contemplated that each sequential operative engagement of a tooth 45 of the plurality of teeth of the gear assembly 40 by a locking pawl 54 can correspond to a predetermined angular rotation of the lobe 42, and thus, the second bending member 44. For example, when a first tooth is operatively engaged by the first locking pawl, the lobe 42 can be rotated by an angle corresponding to the predetermined angular rotation such that the first locking pawl becomes disengaged with the first tooth and the second locking pawl becomes operatively engaged with the first tooth. Similarly, following operative engagement of the first tooth with the second locking pawl, the lobe 42 can be rotated by an angle corresponding to the predetermined angular rotation such that the second locking pawl becomes disengaged with the first tooth and the first locking pawl becomes operatively engaged with a second, adjacent tooth. Thus, it is contemplated that the use of the gear assembly 40 with two locking pawls 54 having engagement portions 55 with different lengths as described herein can effectively function as a single locking pawl coupled to a gear having twice the number of teeth as the disclosed gear assembly. Similarly, it is further contemplated that the use of a gear assembly 40 with two locking pawls 54 can permit a user to advance the gear assembly from a first locked position to a second, sequential locked position by opening or closing the first lever 22 relative to the second lever 32 by a distance that is about one-half the distance necessary to advance the gear assembly from the first locked position to the second locked position using a single locking pawl. As used herein, the term "locked position" refers to a position of the gear assembly in which a tooth of the gear assembly is engaged with the at least one locking pawl 54. Thus, when the at least one locking pawl 54 comprises a first locking pawl and the second locking pawl, a "locked position" refers to a position of the gear assembly in which a tooth of the gear assembly is engaged by one of the first locking pawl and the second locking pawl.

It is further contemplated that the disclosed gear assembly 40 can comprise stronger and larger gear teeth 45 than a gear configured for use with a single locking pawl; consequently, it is contemplated that the teeth of the disclosed gear assembly 40 can be more resistant to wear than the teeth of a gear configured for use with a single locking pawl. In a further aspect, it is contemplated that the use of two locking pawls 54 having engagement portions 55 with different lengths can permit the user to more accurately and precisely produce bends in a surgical implant, particularly bends at angles of less than 10 degrees.

In one aspect, as shown in FIGS. 1-7, the first lever assembly 20 can be configured to receive a surgical implant 60, including, for example and without limitation, a surgical rod. In another aspect, the first bending member 26 can define a bending surface 27. In an additional aspect, the second bending member 44 can be configured to apply a bending force to a portion of the surgical implant 60 upon the angular rotation of the lobe 42 of the gear assembly 40. In this aspect, the second bending member 44 can apply the bending force to the surgical implant 60 upon the angular rotation of the lobe 42 such that the surgical implant is bent at a bending point proximate the bending surface 27 of the first bending member 26.

In another aspect, and with reference to FIG. 2, the first side wall 28 of the bending instrument 10 can have a bottom surface 21. In this aspect, it is contemplated that the second bending member 44 and the first bending member 26 can each be positioned at a height relative to the bottom surface 21 of the first side wall 28. It is further contemplated that the height of the second bending member 44 relative to the bottom surface 21 can be greater than the height of the first bending member 26 relative to the bottom surface. It is still further contemplated that the first and second bending members 26, 44 can be spaced so as to permit bending of short rods and other surgical implants, as well as angled bending proximate the ends of longer rods and other surgical implants. More particularly, it is contemplated that the distance between the first and second bending members 26, 44 can be independent of the force applied by a user to the first and second levers 22, 32 in order to bend a rod or other surgical implant in a desired manner. It is contemplated that the larger the distance between the first and second bending members 26, 24, the smaller the force of the rod will be on the first and second bending members during bending of the surgical implant. However, it is also contemplated that the greater the distance between the first and second bending members 26, 44, the more difficult it can be for a user to create bends proximate an end of a surgical implant. Thus, the spacing of the first and second bending members 26, 44 can be selected based upon a user's preferences for minimizing the amount of force necessary to bend the surgical implant and for permitting bends proximate an end of the surgical implant. It is contemplated that the preferences of the user or a designer can vary depending upon many factors, which can include, without limitation, at least one of the size and material of the surgical implant, the lengths of the first and second levers 22, 32, and the size, strength, and dexterity of the user's hands and fingers. In still a further aspect, the first bending member 26 and the second bending member 44 can be substantially co-planar.

As shown in FIG. 1-7, in an additional, optional aspect, the first lever assembly 20 can further comprise a support member 70 mounted thereon the first side wall 28 of the bending instrument 10. In this aspect, it is contemplated that the support member 70 can extend substantially perpendicularly to the first side wall 28. However, it is contemplated that the support member 70 can be mounted thereon any portion of the bending instrument proximate the distal portions 24, 34 of the first and second levers 22, 32. In another aspect, the support member 70 can be positioned at a height relative to the bottom surface 21 of the first side wall 28. It is contemplated that the height of the support member 70 relative to the bottom surface 21 can be less than the height of the first bending member 26 relative to the bottom surface 21. It is further contemplated that the first bending member 26, the second bending member 44, and the support member 70 can be substantially co-planar. In still another aspect, the support member 70 can be spaced from the first bending member 26 so as to define at least a portion of a receiving channel 72. In this aspect, it is contemplated that the receiving channel 72 can be configured to receive the surgical implant 60.

In another aspect, the bending instrument can optionally comprise a torsion spring in operative communication with the gear assembly 40. In this aspect, it is contemplated that the torsion spring can be biased such that, when the drive pawl 50 and the locking pawls 54 are disengaged from the gear assembly 40, the torsion spring can cause the gear assembly to rotate to a desired position. In exemplary aspects, the desired position can correspond to the initial position and orientation of the gear assembly 40 prior to engagement of the gear assembly by the drive pawl 50.

In a further aspect, the components of the bending instrument can comprise stainless steel. In this aspect, the components of the bending instrument can comprise ASTM 431 stainless steel. It is contemplated that the stainless steel components of the bending instrument can have a Rockwell Hardness value ranging from about 25HRC to about 30HRC. It is further contemplated that each surface of the bending instrument can have Rockwell Hardness values within 4HRC of its mating surfaces. In another aspect, it is contemplated that the components of the bending instrument can comprise titanium. In still another aspect, it is contemplated that the bending instrument can have a smooth surface finish and a reflection-reducing outer coating. It is further contemplated that the surfaces of the bending instrument can be passivated to prevent corrosion. It is also contemplated that the components of the bending instrument can comprise materials that can be conventionally sterilized and that are sufficiently rigid to perform the described operation of the apparatus.

Figure 6:
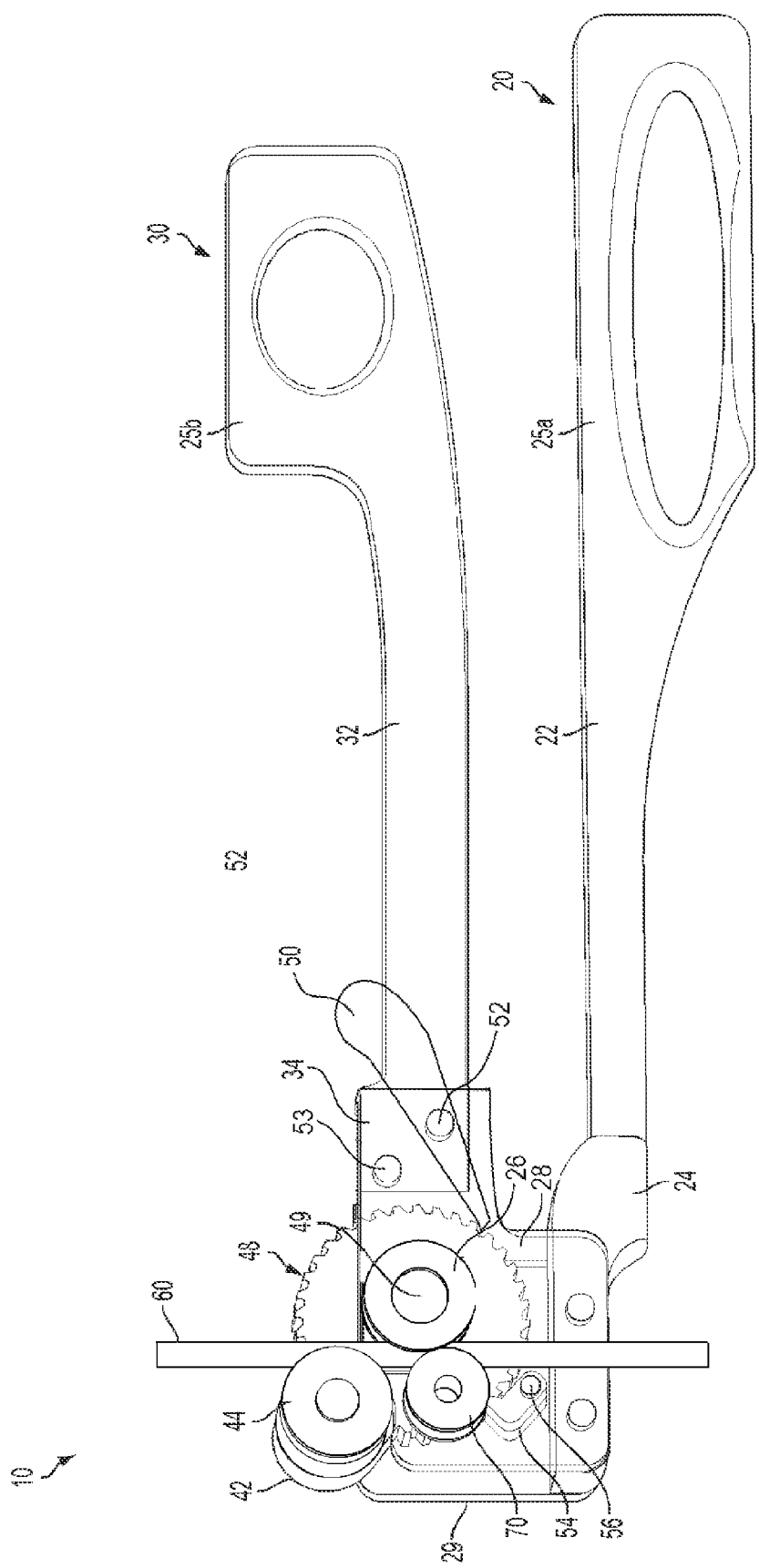
FIG. 6 is a partially transparent, right side view of a modified embodiment of a bending instrument as described herein.

In exemplary aspects, it is contemplated that alternative orientations of the drive pawl 50, as well as alternative pivotal configuration of the second lever 32, can be employed while maintaining the disclosed functionality of the bending instrument 10. In one optional, exemplary aspect, as shown in FIG. 6, the second lever assembly 30 can be shortened while the first and second side walls 28, 29 are extended to overlap with the shortened second lever 32. In this aspect, the openings of the distal end 34 of the second lever 32 are configured to receive conventional pin 53 rather than conventional pin 49. Thus, in this aspect, the second lever 32 is secured to the first and second side walls 28, 29 using conventional pin 53, while conventional pin 49 simply supports the gear assembly 40 in between the first and second side walls. In another aspect, the second lever 32 can be configured for pivotal rotation relative to the first and second side walls 28, 29 as well as the first lever 22. In an additional aspect, and as shown in FIG. 6, it is contemplated that conventional pin 52, which supports the drive pawl 50, can be angularly spaced from conventional pin 53. In a further aspect, it is contemplated that the channel 36 of the second lever 32 can be elongated to accommodate the drive pawl 50, conventional pin 52, and conventional pin 53. As depicted in FIG. 6, it is further contemplated that drive pawl 50 can be elongated and/or curved to extend beyond the channel 36 such that a user can access at least a portion of the drive pawl. In these aspects, it is still further contemplated that the decreased length of the second lever assembly 30 can result in a decrease in the total weight of the bending instrument 10.

In use, the above-described bending instruments can be used in a method of bending a surgical implant. In one aspect, the method of bending the surgical implant can comprise selectively pivoting the second lever relative to the first lever to effect angular rotation of the second bending member of the gear assembly about the common axis and angularly about the first bending member. It is contemplated that the second bending member can be angularly rotated such that the second bending member applies a bending force to a portion of the surgical implant. It is further contemplated that the bending force can be applied to the surgical implant such that the surgical implant is bent at a bending point proximate the bending surface of the first bending member. In another aspect, the step of selectively pivoting the second lever relative to the first lever can comprise sequentially pivoting the second lever from an open position to a closed position until the second bending member is rotated a desired angle. It is contemplated that the desired angle of rotation of the second bending member can range from about 0 degrees to about 90 degrees. Optionally, it is contemplated that the effected desired bending angle can be incrementally achieved with sequential operation of movement between the open and closed positions. In one exemplary aspect, it is contemplated that the opening in the proximal end of one lever can receive the thumb of a hand of the user, while the opening in the proximal end of the other lever can receive one or more of the remaining fingers of the hand of the user. In this aspect, it is contemplated that the sequential operation of movement between the open and closed positions can be achieved by opening and closing of the thumb and fingers of the hand of the user.

Figure 7:
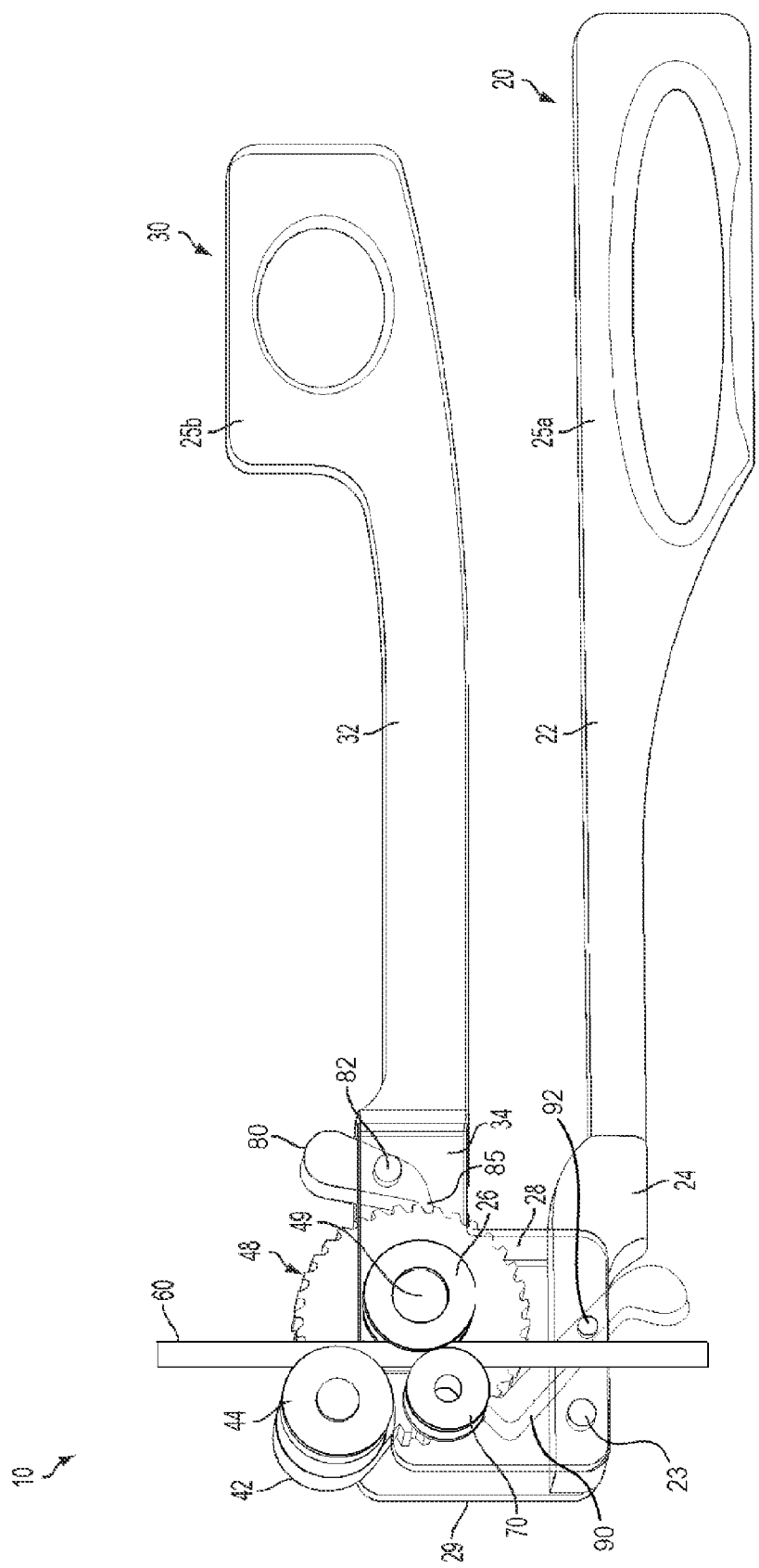
FIG. 7 is a partially transparent, right side view of another modified embodiment of a bending instrument as described herein.

In exemplary aspects, and with reference to FIG. 7, it is contemplated that the first lever 22 of the bending instrument 10 can be configured for rotational movement relative to the second lever 32. In these aspects, it is contemplated that the second lever 32 can be rigidly secured thereto the first and second side walls 28, 29, while the first lever 22 is configured for pivotal rotation relative to the second lever and the first and second side walls. Optionally, in one aspect, the second lever assembly 30, including the second lever 32, and the first and second side walls 28, 29 can be formed as a rigid, one-piece construction. In this aspect, it is contemplated that the one-piece construction of the second lever assembly 30 can provide necessary rigidity while reducing the total weight of the bending instrument 10.

In another aspect, as depicted in FIG. 7, the distal portion 34 of the second lever assembly 30 can define the first side wall 28 and the second side wall 29 of the bending instrument 10. In this aspect, it is contemplated that the second lever assembly 32 can further comprise the first bending member 26, which can be mounted thereon the first side wall 28. It is further contemplated that the first bending member 26 can extend substantially perpendicular to the first side wall 28. In an additional aspect, the distal end 24 of the first lever 22 can define a channel. In one non-limiting example, it is contemplated that the channel of the distal end 24 of the first lever 22 can comprise a U-shaped channel. It is further contemplated that the presence of the channel in the distal end 24 of the first lever 22 can further reduce the total weight of the bending instrument 10 while maintaining the disclosed functionality of the bending instrument. As shown in FIG. 7, in a further aspect, the distal end 24 of the first lever 22 can be configured for positioning between the first and second side walls 28, 29. In this aspect, it is contemplated that a conventional pin 23 can extend between, and be secured thereto, the first and second side walls 28, 29. It is further contemplated that the distal end 24 of the first lever 22 can comprise one or more openings that align with, and are configured to receive, the conventional pin 23.

In one aspect, as shown in FIG. 7, the bending instrument 10 can comprise means for angularly rotating the second bending member 44 of the gear assembly 40 about the common axis $A_C$ and relative to and about the first bending member 26 upon the pivotal rotation of the first lever 22 relative to the second lever 32. It is contemplated that the means for angularly rotating the second bending member 44 can comprise a drive pawl 90 that is sized and shaped for complementary engagement with the gear surface 48 of the gear assembly 40. Optionally, in one aspect, the drive pawl 90 can be rotatably mounted therein the channel of the distal end 24 of the first lever 22. In this aspect, it is contemplated that the drive pawl 90 can define an opening that is configured to receive a conventional pin 92 that extends across the channel of the distal end 24 of the first lever 22 and is secured thereto the distal end of the first lever.

In an additional aspect, the first lever 22 can be configured for pivotal motion relative to the second lever 32 between an open position and a closed position. In this aspect, it is contemplated that, when the first lever 22 is pivoted relative to the second lever 32 from the open position to the closed position, the drive pawl 90 can selectively and drivingly engage a tooth 45 of the gear assembly 40 such that the gear assembly is rotated about the common axis $A_C$ through a defined acute number of degrees. In one aspect, the drive pawl 90 can be biased such that the drive pawl maintains contact with the teeth 45 of the gear assembly 40 as the drive pawl is advanced from one tooth of the gear assembly to consecutive teeth of the gear assembly. In this aspect, the drive pawl 90 can be biased by a spring (not shown) that is configured to rotate the drive pawl about pin 92. In an exemplary, non-limiting aspect, the spring can be a torsion spring.

In another aspect, the bending instrument 10 can comprise means for securely positioning the drive pawl 90 in a disengaged position spaced from the gear assembly 40. In one aspect, it is contemplated that the means for securely positioning the drive pawl 90 in the disengaged position can comprise a conventional spring-ball-detent mechanism. In this aspect, the spring-ball-detent mechanism can be configured to secure the drive pawl 90 in the disengaged position until a user selectively applies a force sufficient to release the spring-ball-detent mechanism and, thereby, permit engagement between the drive pawl and the gear assembly 40. It is contemplated that the means for securely positioning the drive pawl 90 in the disengaged position can comprise any other mechanical mechanism capable of temporarily holding the drive pawl 90 in the disengaged position, including, for example and without limitation, a plunger mechanism, a pop through mechanism, a pin, a ring, and the like. Optionally, the means for securely positioning the drive pawl 90 in the disengaged position can be coupled to the first lever 22.

In an additional aspect, the drive pawl 90 can be operatively coupled to an on/off switch that is moveable about and between an off position and an on position. In this aspect, it is contemplated that a user can direct the drive pawl 90 to engage the gear assembly 40 by movement of the on/off switch from the off position to the on position. In exemplary aspects, it is contemplated that the on/off switch can be configured for contact with a thumb of a user. In yet another aspect, the drive pawl 90 can be operatively coupled to one or more torsion springs that are configured to maintain engagement between the drive pawl and the gear assembly 40 during operation of the bending instrument 10.

As shown in FIG. 7, in another aspect, the means for angularly rotating the second bending member 44 can comprise at least one locking pawl 80 spaced from the drive pawl 90. Optionally, in one aspect, the at least one locking pawl 80 can be mounted between and secured thereto the two spaced side walls 28, 29. In this aspect, it is contemplated that each locking pawl 80 of the at least one locking pawl can define an opening that is configured to receive a conventional pin 82 that extends between, and is secured thereto, the two spaced side walls 28, 29. In a further aspect, the at least one locking pawl 80 can be configured, or otherwise sized and shaped, to selectively operatively engage a portion of the gear surface 48 of the gear assembly 40 as the gear assembly rotates. In this aspect, the at least one locking pawl 80 can operatively engage the gear assembly 40 such that the at least one locking pawl remains engaged with the gear assembly when the first lever 22 is pivoted to the open position.

In an additional aspect, the at least one locking pawl 80 can be operatively coupled to an on/off switch that is moveable about and between an off position and an on position. In this aspect, it is contemplated that a user can direct the at least one locking pawl 80 to engage the gear assembly 40 by movement of the on/off switch from the off position to the on position. It is further contemplated that the on/off switch, which allows for quick, selective engagement or disengagement of the gear assembly 40, can permit a user to more easily produce large-angle bends, as well as small, gradual bends, in a surgical implant 60. In yet another aspect, the at least one locking pawl 80 can be operatively coupled to one or more torsion springs that are configured to maintain engagement between the at least one locking pawl and the gear assembly 40 during operation of the bending instrument 10. It is contemplated that the one or more torsion springs can be positioned such that the gear assembly 40 is returned to a starting position after the gear assembly is released by the at least one locking pawl 80.

In still a further aspect, it is contemplated that the at least one locking pawl 80 can comprise a first locking pawl and a second locking pawl. In this aspect, it is further contemplated that, during rotation of the gear assembly 40, the first locking pawl and the second locking pawl can be configured for sequential alternating engagement of the plurality of teeth 45 of the gear assembly. In an additional aspect, it is contemplated that each tooth 45 of the plurality of teeth of the gear assembly 40 can be angularly spaced from adjacent teeth along the gear surface 48 such that, after a locking pawl 80 of the at least one locking pawl is engaged by the gear assembly and the first lever 22 and the second lever 32 are positioned in the closed position, a user of the bending instrument 10 can move the first and second levers toward the open position to advance the drive pawl 90 one or more teeth along the gear surface. Accordingly, it is contemplated that the angular spacing between adjacent teeth 45 along the gear surface 48 can be selected in view of the ergonomics of opening and closing the first and second levers 22, 32, which can be dependent upon the lengths of the first and second levers and the size, strength, and dexterity of the fingers and hands of the user of the bending instrument 10.

In a further aspect, the plurality of teeth 45 defined by the gear surface 48 of the gear assembly 40 can have a substantially uniform length. In this aspect, it is contemplated that the first locking pawl and the second locking pawl can each have an engagement portion 85 having a length. It is contemplated that the ratio of the length of the engagement portion of the first locking pawl and the length of the engagement portion of the second locking pawl can range from about 1:1 to about 2:1, and more preferably be about 1.5:1. In an exemplary aspect, the teeth 45 of the gear assembly 40 can be spaced from adjacent teeth along the gear surface 48 by a separation distance, and the engagement portion of first locking pawl can be longer than the engagement portion of the second locking pawl by a length corresponding to about one-half the separation distance. In this exemplary aspect, operationally the angle that the gear assembly 40 should be rotated to permit full engagement of the gear assembly by a locking pawl is about one-half the angle formed between adjacent teeth 45 of the gear assembly.

In one exemplary non-limiting aspect, each tooth 45 of the plurality of teeth of the gear assembly 40 can be angularly spaced from adjacent teeth along the gear surface 48 by between about 5 degrees and about 15 degrees, and more preferably by about 10 degrees. In these aspects, it is contemplated that each sequential operative engagement of a tooth 45 of the plurality of teeth of the gear assembly 40 by a locking pawl 80 can correspond to a predetermined angular rotation of the lobe 42, and thus, the second bending member 44. For example, when a first tooth is operatively engaged by the first locking pawl, the lobe 42 can be rotated by an angle corresponding to the predetermined angular rotation such that the first locking pawl becomes disengaged with the first tooth and the second locking pawl becomes operatively engaged with the first tooth. Similarly, following operative engagement of the first tooth with the second locking pawl, the lobe 42 can be rotated by an angle corresponding to the predetermined angular rotation such that the second locking pawl becomes disengaged with the first tooth and the first locking pawl becomes operatively engaged with a second, adjacent tooth. Thus, it is contemplated that the use of the gear assembly 40 with two locking pawls 80 having engagement portions 85 with different lengths as described herein can effectively function as a single locking pawl coupled to a gear having twice the number of teeth as the disclosed gear assembly. It is further contemplated that the disclosed gear assembly 40 can be comprise stronger and larger gear teeth 45 than a gear configured for use with a single locking pawl; consequently, it is contemplated that the teeth of the disclosed gear assembly 40 can be more resistant to wear than the teeth of a gear configured for use with a single locking pawl. In a further aspect, it is contemplated that the use of two locking pawls 80 having engagement portions 85 with different lengths can permit the user to more accurately and precisely produce bends in a surgical implant, particularly bends at angles of less than 10 degrees.

In another aspect, the bending instrument can optionally comprise a torsion spring in operative communication with the gear assembly 40. In this aspect, it is contemplated that the torsion spring can be biased such that, when the drive pawl 90 and the locking pawls 80 are disengaged from the gear assembly 40, the torsion spring can cause the gear assembly to rotate to a desired position. In exemplary aspects, the desired position can correspond to the initial position and orientation of the gear assembly 40 prior to engagement of the gear assembly by the drive pawl 90.

In use, and with reference to FIG. 7, the described bending instrument can be used in a method of bending a surgical implant. In one aspect, the method of bending the surgical implant can comprise selectively pivoting the first lever relative to the second lever to effect angular rotation of the second bending member of the gear assembly about the common axis and angularly about the first bending member. It is contemplated that the second bending member can be angularly rotated such that the second bending member applies a bending force to a portion of the surgical implant. It is further contemplated that the bending force can be applied to the surgical implant such that the surgical implant is bent at a bending point proximate the bending surface of the first bending member. In another aspect, the step of selectively pivoting the first lever relative to the second lever can comprise sequentially pivoting the first lever from an open position to a closed position until the second bending member is rotated a desired angle. It is contemplated that the desired angle of rotation of the second bending member can range from about 0 degrees to about 90 degrees. Optionally, it is contemplated that the effected desired bending angle can be incrementally achieved with sequential operation of movement between the open and closed positions. In one exemplary aspect, it is contemplated that the opening in the proximal end of one lever can receive the thumb of a hand of the user, while the opening in the proximal end of the other lever can receive one or more of the remaining fingers of the hand of the user. In this aspect, it is contemplated that the sequential operation of movement between the open and closed positions can be achieved by opening and closing of the thumb and fingers of the hand of the user.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A bending instrument for bending a rod, comprising:
a first lever assembly comprising a first lever, a first bending member, and a support member, the first lever having a distal portion comprising first and second spaced side walls, the first bending member defining a bending surface, wherein the first bending member and the support member are mounted thereon a distal portion of the first lever and extend substantially perpendicularly from the first side wall of the first lever moving away from the second side wall of the first lever, the first bending member extending along a common axis, wherein the support member is spaced from the first bending member so as to define at least a portion of a receiving channel that is configured to receive the rod;
a second lever assembly comprising a second lever, the second lever having a distal end that defines a channel, wherein the second lever is configured for pivotal motion relative to the first lever;
a gear assembly rotatively coupled to the distal portion of the first lever and configured for rotation about the common axis, the gear assembly defining a lobe and having a second bending member and a gear surface on at least a portion of its peripheral edge, the gear surface defining a plurality of teeth, wherein the second bending member is mounted thereon a portion of the lobe and extends substantially perpendicular to the lobe moving away from the second side wall of the first lever such that the second bending member is substantially co-planar with the first bending member and the support member of the first lever; and
a drive pawl rotatively mounted within the channel of the distal end of the second lever, wherein, upon pivotal rotation of the second lever relative to the first lever, the drive pawl is configured to engage the gear surface of the gear assembly and to rotate the second bending member of the gear assembly about the common axis and angularly about the first bending member,
wherein the second bending member is configured to apply a bending force to a portion of the rod such that the rod is bent at a bending point proximate the bending surface of the first bending member.

2. The bending instrument of claim 1, wherein the second bending member extends along an axis substantially parallel to the common axis.

3. The bending instrument of claim 1, wherein at least a portion of the gear assembly is mounted therein the channel of the distal end of the second lever.

4. The bending instrument of claim 1, wherein the second lever is configured for pivotal motion relative to the first lever between an open position and a closed position, and wherein, when the second lever is pivoted relative to the first lever from the open position to the closed position, the drive pawl is configured to engage a tooth of the gear assembly such that the gear assembly is rotated.

5. The bending instrument of claim 4, further comprising at least one locking pawl spaced from the drive pawl and mounted between and secured thereto the first and second spaced side walls.

6. The bending instrument of claim 5, wherein the at least one locking pawl is configured to operatively engage the gear assembly as the gear assembly rotates such that a locking pawl of the at least one locking pawl remains engaged with the gear assembly when the second lever is pivoted to the open position.

7. The bending instrument of claim 6, wherein the at least one locking pawl comprises a first locking pawl and a second locking pawl.

8. The bending instrument of claim 7, wherein the plurality of teeth defined by the gear surface of the gear assembly have a substantially uniform length, and wherein the first locking pawl and the second locking pawl each have an engagement portion having a length.

9. The bending instrument of claim 8, wherein, during rotation of the gear assembly, the first locking pawl and the second locking pawl are configured for sequential alternating engagement of the plurality of teeth of the gear assembly.

10. The bending instrument of claim 8, wherein the ratio between the length of the engagement portion of the first locking pawl and the length of the engagement portion of the second locking pawl ranges from about 1:1 to about 2:1.

11. The bending instrument of claim 8, wherein each tooth of the plurality of teeth of the gear assembly is angularly spaced from adjacent teeth along the gear surface by between about 5 degrees and about 15 degrees.

12. The bending instrument of claim 1, wherein the rod is a surgical implant.

13. The bending instrument of claim 1, wherein the first side wall of the first lever has a bottom surface, wherein the second bending member and the first bending member are each positioned at a height relative to the bottom surface, and wherein the height of the second bending member relative to the bottom surface is greater than the height of the first bending member relative to the bottom surface.

14. The bending instrument of claim 13, wherein the first lever assembly further comprises a support member mounted thereon a distal portion of the first lever and extending substantially perpendicular to the first side wall of the first lever.

15. The bending instrument of claim 14, wherein the support member is positioned at a height relative to the bottom surface of the first side wall, and wherein the height of the support member relative to the bottom surface is less than the height of the first bending member relative to the bottom surface.

16. The bending instrument of claim 1, wherein the first lever and the second lever each have a proximal end that is configured for engagement by at least a portion of a hand of a user.

17. The bending instrument of claim 1, wherein the receiving channel is configured to receive the rod such that the rod is substantially perpendicular to the common axis and to the first lever.

18. A bending instrument for bending a rod, comprising:
a first lever assembly comprising a first lever, the first lever having a distal end that defines a channel;
a second lever assembly comprising a second lever, a first bending member, and a support member, the second lever having a distal portion comprising first and second spaced side walls that define a channel, the first bending member defining a bending surface, wherein the first bending member and the support member are mounted thereon a distal portion of the second lever and extend substantially perpendicularly from the first side wall of the second lever moving away from the second side wall of the second lever, the first bending member extending along a common axis, wherein the support member is spaced from the first bending member so as to define at least a portion of a receiving channel that is configured to receive the rod, and wherein the first lever is configured for pivotal motion relative to the second lever;
a gear assembly rotatively coupled to the distal portion of the second lever and configured for rotation about the common axis, the gear assembly defining a lobe and having a second bending member and a gear surface on at least a portion of its peripheral edge, the gear surface defining a plurality of teeth, wherein the second bending member is mounted thereon a portion of the lobe and extends substantially perpendicular to the lobe moving away from the second side wall of the first lever such that the second bending member is substantially co-planar with the first bending member and the support member of the first lever, and
a drive pawl rotatively mounted within the channel of the distal portion of the first lever, wherein, upon pivotal rotation of the first lever relative to the second lever, the drive pawl is configured to engage the gear surface of the gear assembly and to rotate the second bending member of the gear assembly about the common axis and angularly about the first bending member,
wherein the second bending member is configured to apply a bending force to a portion of the rod such that the rod is bent at a bending point proximate the bending surface of the first bending member.

19. The bending instrument of claim 18, wherein the first lever is configured for pivotal motion relative to the second lever between an open position and a closed position, and wherein, when the first lever is pivoted relative to the second lever from the open position to the closed position, the drive pawl is configured to engage a tooth of the gear assembly such that the gear assembly is rotated.

20. The bending instrument of claim 19, further comprising at least one locking pawl spaced from the drive pawl and mounted between and secured thereto the first and second spaced side walls.

21. The bending instrument of claim 20, wherein the at least one locking pawl is configured to operatively engage the gear assembly as the gear assembly rotates such that a locking pawl of the at least one locking pawl remains engaged with the gear assembly when the first lever is pivoted to the open position.

22. The bending instrument of claim 18, wherein the receiving channel is configured to receive the rod such that the rod is substantially perpendicular to the common axis and to the second lever.

23. A method of bending a rod, the method comprising:
positioning the rod within a bending instrument, the bending instrument comprising:
a first lever assembly comprising a first lever, a first bending member, and a support member, the first lever having a distal portion comprising first and second spaced side walls, the first bending member defining a bending surface, wherein the first bending member and the support member are mounted thereon a distal portion of the first lever and extend substantially perpendicularly from the first side wall of the first lever moving away from the second side wall of the first lever, the first bending member extending along a common axis, wherein the support member is spaced from the first bending member so as to define at least a portion of a receiving channel that is configured to receive the rod;
a second lever assembly comprising a second lever, the second lever having a distal end that defines a channel, wherein the second lever is configured for pivotal motion relative to the first lever;
a gear assembly rotatively coupled to the distal portion of the first lever and configured for rotation about the common axis, the gear assembly defining a lobe and having a second bending member and a gear surface on at least a portion of its peripheral edge, the gear surface defining a plurality of teeth, wherein the second bending member is mounted thereon a portion of the lobe and extends substantially perpendicular to the lobe moving away from the second side wall of the first lever such that the second bending member is substantially co-planar with the first bending member and the support member of the first lever; and
a drive pawl rotatively mounted within the channel of the distal end of the second lever wherein, upon pivotal rotation of the second lever relative to the first lever, the drive pawl is configured to engage the gear surface of the gear assembly and to rotate the second bending member of the gear assembly about the common axis and angularly about the first bending member; and selectively pivoting the second lever relative to the first lever to effect rotation of the second bending member of the gear assembly about the common axis and angularly about the first bending member such that the second bending member applies a bending force to a portion of the rod to bend the rod at a bending point proximate the bending surface of the first bending member.

24. The method of claim 23, wherein the step of selectively pivoting the second lever relative to the first lever comprises sequentially pivoting the second lever from an open position to a closed position until the second bending member is rotated a desired angle.

* * * * *